United States Patent [19]
Rouget De Gourcez et al.

[11] 3,932,524
[45] Jan. 13, 1976

[54] PROCESS FOR THE PREPARATION OF PHOSPHINE OXIDES AND SULPHIDES

[75] Inventors: Etienne Rouget De Gourcez, Paris; Jean-Claude Mayeux, Bouchet, both of France

[73] Assignee: Societe Nationale des Poudres et Explosifs, France

[22] Filed: Nov. 1, 1972

[21] Appl. No.: 302,638

[30] Foreign Application Priority Data
Nov. 10, 1971 France............................ 71.40229

[52] U.S. Cl.... 260/606.5 P; 260/429 R; 260/429.1; 260/429.2; 260/665 G
[51] Int. Cl.² ........................................... C07F 9/53
[58] Field of Search .................. 260/606.5 P, 665 G

[56] References Cited
UNITED STATES PATENTS

| | | | |
|---|---|---|---|
| 3,080,324 | 3/1963 | Richards et al................. | 260/665 G |
| 3,338,701 | 8/1967 | Weil......................................... | 71/71 |
| 3,347,912 | 10/1967 | Rowe et al. .................. | 260/606.5 P |
| 3,426,087 | 2/1969 | Ashby............................. | 260/665 G |

OTHER PUBLICATIONS

V. Rabl, Chemical Abstracts, Vol. 73, (1970), p. 122123v.
V. Kubala, Chemical Abstracts, Vol. 69, (1968), p. 29031w.
Houben–Weyl, Methoden Der Organischen Chemie, (1962), pp. 158–159.
Houben–Weyl, Methoden Der Organischen Chemie, (1962), p. 172.

Zakharkin et al, Tetrahedron Letters, 1962, pp. 631–633.

*Primary Examiner*—Arthur P. Demers
*Attorney, Agent, or Firm*—Bucknam and Archer

[57] ABSTRACT

A process for the preparation of phosphine oxides or sulphides of the formula:

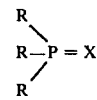

in which R is a linear or branched aliphatic radical containing 5–12 carbon atoms, aralkyl radical selected from the group consisting of lower alkyl of 2–3 carbon atoms substituted by a phenyl group or R is cyclohexyl and X is an oxygen or sulphur atom comprising reacting a halo-compound of the formula R—Hal, in which Hal is chlorine, bromine or iodine, with magnesium to form a Grignard derivative of the formula RMgHal, the reaction being carried out initially in a very small amount of diethyl ether and then in a solvent mixture containing a preponderant amount of an aliphatic or aromatic hydrocarbon, which is liquid at room temperature or triethylamine, adding phosphorus oxychloride or phosphorus sulphochloride to the reaction mixture containing the Grignard derivative, and isolating the phosphine oxide or phosphine sulphide formed by removing the solvent by steam stripping or steam distillation. These compounds are valuable for use in the selective extraction of rare metals.

8 Claims, No Drawings

PROCESS FOR THE PREPARATION OF PHOSPHINE OXIDES AND SULPHIDES

The present invention is concerned with a process for the preparation of phosphine oxides and sulphides of the formula:

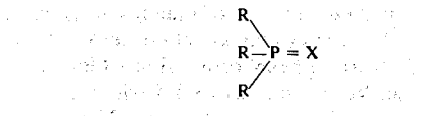

in which R is a linear or branched aliphatic, cyclic or aralkyl radical and X is oxygen or sulphur atom. These compounds are particularly valuable for use in the selective extraction of rare metals, such as lanthanides, actinides and curides; the phosphine oxides and sulphides form complexes with these metals which are easy to isolate.

Processes for the preparation of certain of the phosphine oxides and sulphides of the above formula are known.

One of the known processes (Russian Pat. No. 229,506) for the preparation of phosphine oxides, comprises oxidising phosphines of the formula:

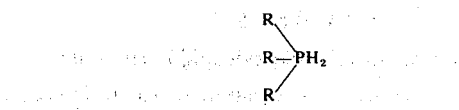

Another known process essentially consists of the reaction of a halogen-containing derivative with phosphorus or phosphorus iodide (Russian Pat. Nos. 149,776 and 149,777).

A third known process for the preparation of phosphine oxides and sulphides comprises reacting phosphorus oxychloride or sulphochloride with a Grignard organo-magnesium compound containing the desired organic group. (U.S. Pat. No. 3,338,701. In this latter process, the preparation of the phosphine oxide or phosphine sulphide is carried out in two main stages; first, the Grignard derivative is prepared in a solvent, such as ethyl ether and tetra-hydrofuran, and then phosphorus oxychloride or sulphochloride is reacted with the Grignard derivative which has been isolated from the solvent. The final product is then isolated by distillation in vacuo.

This latter process suffers from numerous disadvantages which make it difficult to carry out on an industrial scale. The use of ether as the solvent presents a hazard because of its inflammability and its high vapour pressure at ambient temperature. Tetrahydrofuran, on the other hand, is very expensive. Furthermore, the yields obtained in this known process do not exceed 50%.

Additionally, the purification of the final product by distillation in vacuo requires costly apparatus. This operation must be carried out at a temperature of from 150°C to 200°C under a pressure of less than 0.5 mm Hg. The distillation under reduced pressure also takes a long time.

We have now developed a process for the preparation of phosphine oxides and sulphides which is simpler and less costly to carry out and which enables high yields to be obtained, whilst being realisable on an industrial scale.

According to the present invention, we provide a process for the preparation of phosphine oxides or sulphides of the formula:

in which R is a linear or branched aliphatic, cyclic or aralkyl radical and X is an oxygen or sulphur atom, which comprises reacting a halo-compound of the formula R-Hal, in which Hal is a halogen atom, with magnesium to form a Grignard derivative of the formula RMgHal, said reaction being carried out initially in a very small amount of diethyl ether and then in a solvent mixture containing a preponderant amount of an aliphatic or aromatic hydrocarbon or a tertiary amine, adding phosphorus oxychloride or phosphorus sulphochloride to the reaction mixture containing the Grignard derivative, and isolating the phosphine oxide or phosphine sulphide formed by removing the solvent by steam stripping or steam distillation.

A preferred aliphatic hydrocarbon for use as the major solvent in the solvent mixture is octane; preferred aromatic hydrocarbons for this purpose are benzene, toluene and xylene; and a preferred tertiary amine for this purpose is triethylamine.

The mixture obtained after the addition of phosphorus oxychloride or sulphochloride is preferably heated to boiling temperature under reflux. The organic phase of the reaction mixture obtained after the completion of the reaction of the Grignard derivative with the phosphorus oxychloride or sulphochloride is preferably extracted with water prior to removal of the solvent.

The particular advantages of the present process are that the formation of the Grignard derivative is carried out in a solvent mixture which largely consists of a low cost, low hazard solvent and that the use of such solvents enables the final product to be purified by operations which are simple and which can readily be carried out on an industrial scale, that is steam stripping or steam distillation.

Certain of the phosphine sulphides of the above formula which can be prepared by the process according to the invention, are novel, viz.
 tri-decylphosphine sulphide
 tri-dodecylphosphine sulphide
 tri-phenylethylphosphine sulphide
 tri-phenylpropylphosphine sulphide
 tri-(3,5,5-trimethylhexyl)-phosphine sulphide,
and these novel compounds form another aspect of the present invention.

In order that the invention may be more fully understood, the following examples are given by way of illustration only:

EXAMPLE 1

Preparation of tri-octylphosphine oxide

A solution of 44.5 g of octyl chloride in 300 cc of xylene was added dropwise to 12 g of degreased and dry magnesium immersed in a few cc of anhydrous diethyl ether, whilst heating until the reaction started. When the reaction had started, the octyl chloride was added in the cold. When all the octyl chloride solution had been added, stirring was continued for about 1 hour further. 13.8 g of phosphorus oxychloride were then added in the cold. The mixture was then heated to boiling under reflux for 2 hours 30 minutes. The solution was hydrolysed by the addition of 1 litre of water acidified with 100 cc of HCl. The organic phase was decanted, washed with distilled water and neutralised with sodium bicarbonate. After decanting, the organic phase was recovered and then steam-distilled or steam-stripped to remove the solvent without distilling the product. A white solid, trioctylphosphine oxide, was obtained.

The yield of the reaction was 80% relative to the octyl chloride.

The product obtained melted at 50°C. The main absorption bands in the infra-red were at 1,160 cm$^{-1}$ and 2,880 cm$^{-1}$.

In nuclear magnetic resonance, the following peaks were found: 0.86 ppm ($CH_3$) and 1.28 ppm ($CH_2$).

Elementary analysis gave the following results:

| Element determined | %, theoretical | % found |
| --- | --- | --- |
| P | 8.05 | 8.25 |
| C | 74.5 | 72.30 |
| H | 13.25 | 13.09 |
| Cl | 0 | 0 |

EXAMPLE 2

Preparation of tricyclohexylphosphine oxide

The same procedure as in Example 1 was followed. The materials used were 11 g of magnesium, a solution of 35 g of cyclohexyl chloride in 300 cc of octane, and 13.8 g of phosphorus oxychloride.

A white solid, tricyclohexylphosphine oxide, was obtained, which could be recrystallised from toluene.

The product melted at 212°C.

The principal absorption bands in the infra-red were at 1,140 cm$^{-1}$, 2,850 cm$^{-1}$ and 2,900 cm$^{-1}$.

EXAMPLE 3

Preparation of tri-phenylphosphine sulphide

The same procedure as in Example 1 was followed. The materials used were 11 g of magnesium, a solution of 56 g of phenylethyl bromide in 300 cc of triethylamine, and 13.8 g of phosphorus oxychloride.

A white solid, triphenylethylphosphine oxide, was obtained, which could be recrystallised from ether.

The yield obtained was 70% relative to the bromo-ethylbenzene.

The product melted at 56°C.

The principal absorption bands in the infrared were at 1,160 cm$^{-1}$, 2,920 cm$^{-1}$ and 3,000 cm$^{-1}$.

The following peaks were found in nuclear magnetic resonance: 2.7 ppm ($a$), 1.8 ppm ($b$) and 7.1 ppm ($c$): (($b$) and ($c$) denoted the groups indicated in the formula below:

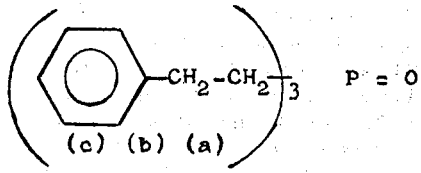

EXAMPLE 4

Preparation of tri-(3,5,5-trimethylhexyl)-phosphine sulphide

The same procedure as in Example 1 was followed, the phosphorus oxychloride being replaced by phosphorus sulphochloride.

The materials used were: 11 g of magnesium, a solution of 48 g of 3,5,5-trimethylhexyl chloride in 300 cc of toluene, and 15 g of phosphorus sulphochloride.

A syrupy colourless liquid, tri-(3,5,5-trimethyl-hexyl)-phosphine sulphide, was obtained. This liquid boiled at 180°C under a pressure of 0.05 mm Hg.

The principal absorption bands in the infrared were at 760 cm$^{-1}$, 2,850 cm$^{-1}$ and 2,900 cm$^{-1}$.

The following peaks were found in nuclear magnetic resonance: 3.5 ppm (triplet) ($a$), 1.7 ppm ($b$) and 1 ppm ($c$); ($a$), ($b$) and ($c$) denoted the groups indicated in the formula below:

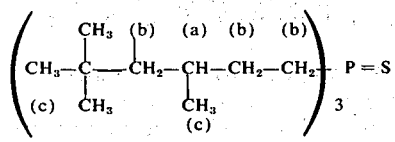

EXAMPLE 5

Preparation of tricyclohexylphosphine sulphide

The same procedure as in Example 1 was followed, the phosphorus oxychloride being replaced by phosphorus sulphochloride. The materials used were: 11 g of magnesium, a solution of 35 g of cyclohexyl chloride in 300 cc of cumene, and 15 g of phosphorus sulphochloride.

A brown solid, tricyclohexylphosphine sulphide, was obtained. This product boiled at 150°C under a pressure of 0.05 mm Hg.

The principal absorption bands in the infra-red were at: 760 cm$^{-1}$, 2,850 cm$^{-1}$ and 2,900 cm$^{-1}$.

Two peaks, at 1.4 and 1.9 ppm, were found in nuclear magnetic resonance.

EXAMPLE 6

Preparation of triphenylpropylphosphine sulphide

The same procedure as in Example 1 was followed, the phosphorus oxychloride being replaced by phosphorus sulphochloride. The materials used were: 11 g of magnesium, a solution of 60 g of phenylpropyl bromide in 300 cc of xylene, and 15 g of phosphine sulphochloride.

A white solid, triphenylpropylphosphine sulphide was obtained. This product could be recrystallised from ethanol, and melted at 88°C.

The principal infra-red absorption bands were at 750 cm$^{-1}$ and 3,000 cm$^{-1}$.

The following peaks were found in nuclear magnetic resonance: 7.5 ppm ($a$), 2.65 ppm ($b$), 1.9 ppm ($c$) and 1.78 ppm ($d$); ($a$), ($b$), ($c$) and ($d$) denoted the groups incicated in the following formula:

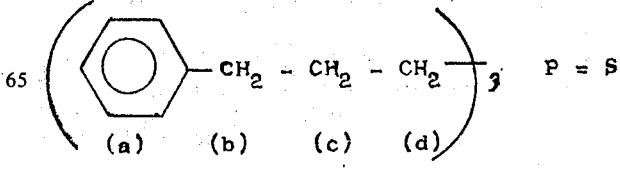

Some characteristic physical properties of phosphine sulphides according to the invention are given below:

| Nomenclature | Appearance | Boiling Point | Melting Point |
|---|---|---|---|
| Tri-pentylphosphine sulphide | colourless liquid | 150°C/0.05 mm Hg | — |
| Tri-decylphosphine sulphide | white crystals | — | 73°C |
| Tri-dodecylphosphine sulphide | white crystals | — | 77°C |
| Tri-phenylethyl-phosphine sulphide | colourless liquid | 92°C/10 mm Hg | — |
| Tri-phenylpropyl-phosphine sulphide | white crystals | — | 88°C |
| Tri-(3,5,5-trimethyl-hexyl)-phosphine sulphide | colourless liquid | 180°C/0.05 mm Hg | — |
| Tri-Cyclohexylphosphine sulphide | brown solid | 150°C/0.06 mm Hg | — |

The phosphine oxides and sulphides of the above formula find their principal industrial application in the extraction of metals. They are capable of forming complexes with, and thus extracting, practically all the metals of the periodic classification and, in particular, the rare metals, such as the lanthanides, the actinides and curides.

The complexes formed are of the type:
MA . $n$ (R$_3$P = X)

M being the metal bound as a complex, A an anion and n a number depending on the co-ordination of the metal M.

An example illustrating the extraction of uranium with tri-pentylphosphine sulphide is given below:

EXAMPLE 7

A mineral containing uranium oxide was treated with nitric acid to form uranyl nitrate:
UO$_2$(NO$_3$)$_2$ This uranyl nitrate formed the following complex with tri-pentylphosphine sulphide:
UO$_2$(NO$_3$)$_2$.2(CH$_3$—(CH$_2$)$_{\overline{4}}$ P = S This complex could be readily isolated by conventional separation methods.

What we claim is:

1. A process for the preparation of phosphine oxides or sulphides of the formula:

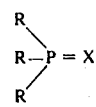

in which R is a linear or branched aliphatic radical containing 5 – 12 carbon atoms, aralkyl radical selected from the group consisting of lower alkyl of 2 – 3 carbon atoms substituted by a phenyl group or R is cyclohexyl and X is an oxygen or sulphur atom which comprises reacting a halo-compound of the formula R—Hal, in which Hal is chlorine, bromine or iodine, with magnesium to form a Grignard derivative of the formula RMgHal, said reaction being carried out initially in a very small amount of diethyl ether and then in a solvent mixture containing a preponderant amount of an aliphatic or aromatic hydrocarbon, which is liquid at room temperature or triethylamine, adding phosphorus oxychloride or phosphorus sulphochloride to the reaction mixture containing the Grignard derivative, and isolating the phosphine oxide or phosphine sulphide formed by removing the solvent by steam stripping or steam distillation.

2. A process according to claim 1, in which the aliphatic hydrocarbon solvent is octane.

3. A process according to claim 1, in which the aromatic hydrocarbon solvent is benzene, toluene, xylene or cumene.

4. A process according to claim 1, in which, after addition of the phosphorus oxychloride or sulphochloride, the reaction mixture is heated to boiling under reflux.

5. A process according to claim 1, in which after completion of the phosphine oxide or sulphide-forming reaction and prior to removal of the solvent, the organic phase of the reaction mixture is washed with water.

6. Tri-phenylethylphosphine sulphide.

7. Tri-phenylpropylphosphine sulphide.

8. Tri-(3,5,5-trimethylhexyl)-phosphine sulphide.

* * * * *